United States Patent [19]

Cashen

[11] 4,002,668
[45] Jan. 11, 1977

[54] METHOD OF PRODUCING ANHYDROUS CRYSTALLINE REACTION PRODUCTS OF FORMALDEHYDE AND METHYL-, ETHYL CARBAMATE

[75] Inventor: Norton A. Cashen, Metairie, La.

[73] Assignee: The United States of America as represented by the Secretary of Agriculture, Washington, D.C.

[22] Filed: May 16, 1975

[21] Appl. No.: 578,298

[52] U.S. Cl. .............................. 260/482 C; 8/187
[51] Int. Cl.² ...................................... C07C 125/06
[58] Field of Search ....................... 260/482 C, 72 B

[56] References Cited

UNITED STATES PATENTS

| | | | |
|---|---|---|---|
| 3,391,181 | 7/1968 | Scheuerl | 260/482 C |
| 3,556,713 | 1/1971 | Kullman | 260/482 C |
| 3,723,058 | 3/1973 | Reinhardt | 260/482 C |
| 3,723,377 | 3/1973 | Spangler | 260/72 B |
| 3,749,751 | 7/1973 | Pai | 260/482 C |

*Primary Examiner*—Anton H. Sutto
*Assistant Examiner*—Michael Shippen
*Attorney, Agent, or Firm*—M. Howard Silverstein; Salvador J. Cangemi; David G. McConnell

[57] ABSTRACT

The instant invention relates to a method for the preparation and isolation of anhydrous crystalline dimethylolated methyl-, and —ethyl carbamate by lyophilization. Further, the instant invention is a dimethylolated methyl-, and ethyl carbamate, the chemical entity of which consists of an increased formaldehyde to nitrogen ratio, which is essentially free of free formaldehyde.

The dimethylol methyl-, and ethyl carbamates are represented by the general formula $ROCON(CH_2OH)_n$, with $n$ being 2, and in which R is an aliphatic or modified aliphatic group.

2 Claims, No Drawings

METHOD OF PRODUCING ANHYDROUS CRYSTALLINE REACTION PRODUCTS OF FORMALDEHYDE AND METHYL-, ETHYL CARBAMATE

FIELD TO WHICH INVENTION RELATES

This invention relates to the chemical finishing of cellulosic textiles. More specifically, it relates to a method of isolating dimethylolated methyl-, and ethyl carbamates. Specifically, a technique known as lyophilization is used for dehydrating aqueous formulations of said methylolated aliphatic monocarbamates. Lyophilization is the act of drying in a frozen state under high vacuum, such as dehydration by subliming from solid or frozen state to vapor state to frozen or solid state.

THE PRIOR ART

In the prior art, means have been proposed for producing an aqueous solution of water-soluble carbamate-formaldehyde condensates, formed in aqueous alkaline solutions containing 2.2 moles of formaldehyde and 1.0 mole of alkyl carbamate.

Another approach for preparing anhydrous dimethylolated aliphatic carbamates is taught by the fusion method of Scheuerl, U.S. Pat. No. 3,391,181, dated July 2, 1968. This process requires the admixing of an essentially anhydrous reaction mixture of alkyl carbamate containing at least two methylolatable amido hydrogens selected from the group consisting of monoalkyl carbamates and alkylene biscarbamates, paraformaldehyde in an amount corresponding to from about 0.9 to about 1.1 equivalent weight of paraformaldehyde for each amido hydrogen atom in said carbamates, and sufficient basic catalyst to maintain the pH from about 8.0 to about 11.0 during the reaction. The reaction slurry is heated between about 50° C to about 85° C until a substantial quantity of amorphous dimethylolated product is produced and the amorphous solid contained therein is isolated.

Frick and Reinhardt, American Dyestuff Reporter, Vol. 56, No. 9, page 41, Apr. 24, 1967, have taught that an agent can be prepared which releases less formaldehyde fumes in durable press finishing by using a lower molar ratio of formaldehyde to carbamate in preparation. However, this improvement is achieved at the expense of obtaining a finish with a lower ratio of HCHO/carbamate, resulting in a finish which is inherently conducive to high chlorine damage.

Chemical methods have been disclosed by Reid, Kullman, and Reinhardt, Proceedings of the Ninth Cotton Utilization Research Converence, Apr. 30-May 2, 1969, New Orleans, La. to decrease free formaldehyde in treatment solutions of methylolated carbamate finishing agents. This method has resulted in undesirable colateral effect on the finished fabric.

Kullman, et al., J. Text. Chem. Color., Vol. 3, No. 12, pp. 35–36, Dec. 1971, have disclosed a method for the reduction of free formaldehyde in sensitized dimethylol alkyl carbamate treated fabrics, by aerating said fabric with moist air or steam, which releases or carries the free formaldehyde.

Lastly, it has been disclosed by Panemangalore, U.S. Pat. No. 3,749,751, a method for the reduction of free formaldehyde in an aqueous solution of methylolated carbamates by contacting the aqueous solution with a nitrogenous carbonyl compound having a CC(O)N(H) group. This process is commonly referred to as a formaldehyde scavenger type chemical system, that consequently results in an increased monomethylolated carbamate content, with an inherent susceptibility to chlorine damage.

OBJECT OF THE INVENTION

It is an object of this invention to provide a method of isolating in the crystalline state, anhydrous dimethylol methyl- and ethyl carbamate, that are substantially void of free formaldehyde.

It is a further object of this invention to produce crystalline dimethylolated methyl-, and ethyl carbamate with improved $CH_2O/N$ ratios in the final product, which is substantially free of unreacted formaldehyde.

Further, it is an object of this invention to produce a finishing agent for cellulose for cellulose-containing textiles, comprised of methylolated alkyl carbamates, which affords a means of chemically finishing said textiles:

a. with no limitations on the amount of water in the finishing systems, i.e., infinite emulsion combinations.

b. with these crystalline agents in totally anhydrous carbamate solubilizing finishing systems, such as systems employing pure or mixed organic solvents...with ecological implications.

c. without the need of preparing the carbamate finishing agents (1) with lower ratios of NCHO/N, (2) with containment of chemical scavengers, and (3) without the need of post treatments of the finished fabrics by aeration or steam - in order to minimize free formaldehyde in sensitized or fully cured carbamate finished fabrics.

d. without the risk of hydrolyzing the finish of a fully cured cellulose or cellulose containing textile by a post steaming treatment.

HOW THE OBJECTS ARE ACHIEVED

The objective of producing a crystalline methylolated monoalkyl carbamate with an increased formaldehyde to nitrogen ratio is achieved by the dehydration or sublimation of a frozen aqueous preparation (not exceeding 10% solids) by lyophilization at high vacuum the equivalent of 1 micron of Hg. The consequential objectives are achieved by having a product available which is an effective cellulose chemical finishing agent, that can be used as such with essentially no attendant free formaldehyde.

SUMMARY OF THE INVENTION

The detailed description and specific examples that follow are provided merely to illustrate the invention as well as preferred embodiments. These illustrations should not be construed as limiting the scope of the instant invention in any manner whatever. Numerous changes and modifications will become apparent to those skilled in the art.

EXAMPLE 1

Admix an aqueous reaction mixture of paraformaldehyde and a commercial grade of methyl carbamate in a molar ratio of 2.2 to 1.0, to give a total solids content of fifty percent, and sufficient basic catalyst to maintain a pH of 10.0. Either heat for thirty minutes or allow to stand at ambient temperature for 24 hours, after which adjust pH to 5.5 with a mineral acid, as taught in U.S. Pat. No. 3,219,632.

Adjust this aqueous solution of dimethylol methyl carbamate by dilution to the equivalent of ten percent solids or less. Transfer 150 grams aliquot of this solution to a 500 ml round bottom flask and quick freeze by rotating in acetone-frozen $CO_2$ bath. Evacuate the vessel to approximately one-micron Hg pressure, and lyophilize for twenty-four hours. Sublimation of the frozen water occurs until an initial trace contaminant, namely formic acid, increases in concentration with consequential depression of freezing point...this permits a thaw before the sublimation of 100% water occurs, resulting in the formation of a highly viscous hydrous syrup of the dimethylol methyl carbamate. During the initial 24-hour lyophilization, sufficient contaminant is volatilized and removed so that repeat 24-hour lyophilization, after re-dilution to 10% solids, results in crystal seeding in a syrupy residue — with the initial seeding occurring, if the vessel is placed where the temperature is reduced to 18° C, complete crystallization takes place.

EXAMPLE 2

With the use of ethyl carbamate, procedure is exactly that of Example 1, excepting upon completion of second 24-hour lyophilization, complete crystallization occurs without the need of decreasing the temperature below ambient. The product obtained by this procedure was anhydrous, and crystalline as having been determined anisotropic under light microscopy. This product was one of increased formaldehyde to nitrogen ratio as determined by nuclear magnetic resonance method:

| Method of | PHYSICAL state and HCHO/N Physical state | Molar ratio HCHO/N |
|---|---|---|
| D. R. Scheuerl | amorphous | 1.76 |
| N. A. Cashen | Crystalline | 1.83 |

What I claim is:

1. A process for preparing in the crystalline state, dimethylol methyl carbamate, the process which comprises:
   a. admixing an aqueous reaction mixture of paraformaldehyde and methyl carbamate in a molar ratio to 2.2 to 1.0, to give a total solids content of 25–50%, and sufficient basic catalyst to maintain a pH of 10.1;
   b. allowing the solution from (a) to stand for 30 minutes to 24 hours at temperatures varying from ambient to 65° C;
   c. adjusting the solution from (b) to a pH of 5.5 with a mineral acid;
   d. adjusting the solution from (c) with water to a solids concentration no greater than ten weight percent;
   e. lyophilizing the frozen solution from (d) for about twenty-four hours;
   f. diluting the lyophilized product from (e) with water to ten percent solids, and lyophilizing the diluted product;
   g. reducing the temperature of the partially crystalline residue of (f) to about 18° C.

2. A process for preparing in the crystalline state, dimethylol ethyl carbamate, comprising:
   a. admixing an aqueous reaction mixing of paraformaldehyde and ethyl carbamate in a molar ratio of 2.2 to 1.0 to give a total solids content of 25–50% and sufficient basic catalyst to maintain a pH of 10.0;
   b. allowing the solution from (a) to stand for 30 minutes to 24 hours at temperatures varying from ambient to 65° C;
   c. adjusting the solution from (b) to a pH of 5.5 with a mineral acid;
   d. adjusting the solution from (c) with water to a solids concentration no greater than ten weight percent;
   e. lyophilizing the frozen solution from (d) for about twenty-four hours; and
   f. diluting the lyophilizing product from (e) with water to ten percent solids, and lyophilizing the diluted product.

* * * * *